United States Patent
Michel et al.

[11] Patent Number: 6,002,062
[45] Date of Patent: Dec. 14, 1999

[54] PROCESS FOR THE PREPARATION OF ETHYNYLCYCLOPROPANE

[75] Inventors: Dominique Michel, Susten; Paul Hanselmann, Brig-Glis, both of Switzerland

[73] Assignee: Lonza AG, Gampel/Valais, Switzerland

[21] Appl. No.: 09/204,503

[22] Filed: Dec. 4, 1998

[30] Foreign Application Priority Data

Dec. 10, 1997 [CH] Switzerland ............................. 2842/97

[51] Int. Cl.$^6$ ...................................................... C07C 2/00
[52] U.S. Cl. ........................ 585/534; 585/357; 585/638; 585/639; 585/640; 585/20
[58] Field of Search ..................... 585/357, 534, 585/638, 639, 640, 20

[56] References Cited

U.S. PATENT DOCUMENTS 4,395,580  7/1983  Juguin et al. ............................ 585/639

FOREIGN PATENT DOCUMENTS

WO 96/22955  8/1996  WIPO.
WO 98/40333  9/1998  WIPO.

OTHER PUBLICATIONS

"Fine Chemistry with Small Rings–Cyclopropyl Compounds for Efficient Synthesis", New Aspects Org.Chem II, Proc. Int. Kyoto Conf. 5th (60 UNAD); pp. 181–213, 1992 No Month.

Taskinen, E., Acta Chemica Scandinavica. Series B.—Organic Chemistry and Biochemistry, vol. 28, No. 3, (1974), pp. 357 to 366, (Taskinen) –No Month.

*Primary Examiner*—Walter D. Griffin
*Assistant Examiner*—Nadine Preisch
*Attorney, Agent, or Firm*—Fisher, Christen & Sabol

[57] ABSTRACT

Ethynylcyclopropane is prepared from (1,1-dimethoxyethyl)cyclopropane by a two-stage elimination of methanol. Ethynylcyclopropane is an intermediate in the synthesis of pharmaceutically active ingredients, for example, antiviral agents.

9 Claims, No Drawings

PROCESS FOR THE PREPARATION OF ETHYNYLCYCLOPROPANE

BACKGROUND OF THE INVENTION

1. Field of the Invention

The invention relates to a process for the preparation of ethynylcyclopropane of the formula:

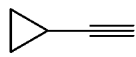
I

Ethynylcyclopropane is an intermediate in the synthesis of pharmaceutically active ingredients, for example, antiviral agents for combating HIV infections (international Published Patent Application No. WO 96/22955).

2. Background Art

A known synthesis of ethynylcyclopropane starts from 1-bromo-3-chloropropane, which is reacted with sodium acetylide to give 5-chloro-1-pentyne. The latter compound is cyclized with n-butyllrthium to give the desired compound. A disadvantage of such process is that it requires low temperatures. Another known process starts from cyclopropyl methyl ketone, which is first converted into (1,1-dichloroethyl)cyclopropane. The desired product is obtained from the latter compound by eliminating two molecules of hydrogen chloride. It is a disadvantage of such process that the preparation of the geminal dichloride requires drastic conditions (e.g., $PCl_5$). In addition, both of the prior art processes mentioned produce at least 2 mols of halide waste per mole of product.

BROAD DESCRIPTION OF THE INVENTION

The object of the Invention is to provide an alternative process for the preparation of ethynylcyclopropane which does not require low temperatures and which produces little waste.

According to the invention, this object is achieved by the process according to the invention.

It has been found that methanol can be eliminated from (1,1-dimethoxyethyl)cyclopropane of the formula:

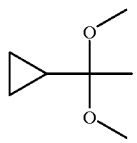
II in two stages, first, giving the enol ether (1-methoxyethenyl) cyclopropane of the formula:

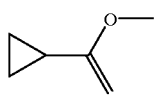
III and then the desired product (1).

(1,1-Dimethoxyethyl)cyclopropane can be prepared in a known manner from commercially available cyclopropyl methyl ketone and trimethyl orthoformate.

The first stage of the process according to the invention is preferably carried out under heterogeneous catalysis. This has the advantage that the catalyst can be removed easily and, if desired, reused. The heterogeneous catalyst is particularly preferably aluminum oxide, especially the "neutral" aluminum oxide available commercially for chromatographic purposes.

The second stage of the process according to the invention is advantageously carried out in the presence of at least two equivalents of a strong base. In this case, the two reaction products ethynylcyclopropane (I) and methanol are initially produced in the deprotonated form as acetylide and alkoxide. The acetylide is protonated again to give ethynylcyclopropane during workup.

Particularly preferred strong bases are alkyllithium compounds, such as, n-butyllithium or tert-butyllithium.

DETAILED DESCRIPTION OF THE INVENTION

The examples below illustrate how the process according to the invention is carried out, without limiting it thereto.

EXAMPLE 1

(1,1-Dimethoxyethyl)cyclopropane (II)

A mixture of 50 g (0.59 mol) of cyclopropyl methyl ketone, 82 g (0.77 mol) of trimethyl orthoformate, 200 ml of methanol and 0.25 g of p-toluenesulfonic acid was stirred at room temperature for 2 hours, and then 0.15 g of sodium methoxide was added. Then, under reduced pressure, the methanol was first distilled off (at about 400 mbar) and, finally (at about 250 mbar), the product (II) as a colorless liquid.

EXAMPLE 2

(1-Methoxyethenyl)cyclopropane (III)

2 g of aluminum oxide (neutral, 100–125 mesh) was added to the (1,1-dimethoxyethyl)cyclopropane (II) from Example 1, and the mixture was heated in a distillation apparatus until a mixture of methanol and III passed over at from 63° to 94° C. This mixture was collected in a receiver containing 40 ml of water and 40 ml of decalin. After the reaction had ended, the two phases were separated, and the organic phase was dried with sodium sulfate. The product (III) was isolated by distillation. The yield of the product was 30 g (51 percent, based on cyclopropyl methyl ketone) in the form of a colorless liquid. The boiling point of the product was 108° to 115° C.

EXAMPLE 3

Ethynylcyclopropane (I) 140 ml (0.22 mol) of a 1.6 M solution of n-butyllithium in hexane was reduced by evaporation under reduced pressure. A solution of 10 g (0.1 mol) of (1-methoxyethenyl)cyclopropane (III) in 60 ml of decalin was then added, and the mixture was heated at 110° C. for 5 hours. The mixture was then cooled to 0° C., and 50 ml of water was then added. The aqueous phase was separated off, and the organic phase was dried over sodium sulfate. The product was isolated by distillation. The yield of the product was 2.6 g (39 percent) of a colorless liquid. The boiling point of the product was 50° to 51° C.

What is claimed is:

1. A process for the preparation of ethynylcyclopropane of the formula:

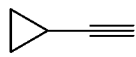

comprising, in a first stage, contacting (1,1-dimethoxyethyl) cyclopropane of the formula:

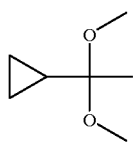

with a catalyst to accomplish the elimination of methanol to give (1-methoxyethenyl)cyclopropane of the formula:

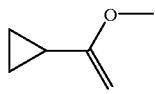

and, in a second stage, subjecting said (1-methoxyethyl) cyclopropane of the formula III to further methanol elimination.

2. The process according to claim 1, wherein the first stage is carried out under heterogeneous catalysis.

3. The process according to claim 2, wherein the heterogeneous catalyst is aluminum oxide.

4. The process according to claim 3, wherein the second stage is carried out in the presence of at least two equivalents of a strong base.

5. The process according to claim 4, wherein the strong base is n-butyllithium or tert-butyllithium.

6. The process according to claim 1, wherein the second stage is carried out in the presence of at least two equivalents of a strong base.

7. The process according to claim 6, wherein the strong base is n-butyllithium or tert-butyllithium.

8. The process according to claim 2, wherein the second stage is carried out in the presence of at least two equivalents of a strong base.

9. The process according to claim 8, wherein the strong base is n-butyllithium or tert-butyllithium.

* * * * *